United States Patent [19]

Anjur et al.

[11] Patent Number: 5,624,423
[45] Date of Patent: Apr. 29, 1997

[54] ABSORBENT ARTICLE HAVING BARRIER MEANS AND MEDIAL BULGE

[75] Inventors: Sowmya S. Anjur, Appleton; Joseph DiPalma, Neenah, both of Wis.

[73] Assignee: Kimberly-Clark Corporation, Neenah, Wis.

[21] Appl. No.: 348,270

[22] Filed: Nov. 30, 1994

[51] Int. Cl.$^6$ .......................... A61F 13/15; A61F 13/20
[52] U.S. Cl. .................. 604/385.1; 604/385.2; 604/369; 604/378; 604/379
[58] Field of Search ................. 604/385.1, 378, 604/369, 385.2, 379

[56] References Cited

U.S. PATENT DOCUMENTS

| | | | |
|---|---|---|---|
| Re. 33,351 | 9/1990 | Papajohn | 604/387 |
| 907,784 | 12/1908 | Green | |
| 1,192,439 | 7/1916 | Luellen | |
| 1,946,626 | 2/1934 | Jurgensen | 128/290 |
| 2,043,325 | 6/1936 | Jackson, Jr. | 128/284 |
| 2,064,431 | 12/1936 | Jurgensen | 128/290 |
| 2,092,346 | 9/1937 | Arone | 128/284 |
| 2,331,355 | 10/1943 | Strongson | 128/290 |
| 2,566,451 | 9/1951 | Julien | 128/290 |
| 2,683,457 | 7/1954 | Cunningham | 128/290 |
| 2,747,575 | 5/1956 | Mercer | 128/290 |
| 2,973,760 | 3/1961 | Dudley | 128/287 |
| 3,121,427 | 2/1964 | Mosier | 128/284 |
| 3,183,909 | 5/1965 | Roehr | 128/290 |
| 3,192,109 | 6/1965 | Mosier | 128/289 |
| 3,262,451 | 7/1966 | Morse | 128/290 |
| 3,444,859 | 5/1969 | Kalwaites | 128/284 |
| 3,572,342 | 3/1971 | Lindquist et al. | 128/287 |
| 3,575,174 | 4/1971 | Mogor | 128/290 |
| 3,595,235 | 7/1971 | Jespersen | 128/284 |
| 3,769,979 | 11/1973 | Freney | 128/290 R |
| 3,844,288 | 10/1974 | Kiela | 128/287 |
| 3,857,394 | 12/1974 | Alemany | 128/260 |
| 3,865,112 | 2/1975 | Roeder | 128/290 R |
| 3,888,254 | 6/1975 | Hendricks | 128/290 R |
| 4,031,897 | 6/1977 | Graetz | 128/286 |
| 4,046,147 | 9/1977 | Berg | 128/290 R |
| 4,079,739 | 3/1978 | Whitehead | 128/290 R |
| 4,184,498 | 1/1980 | Franco | 128/290 R |
| 4,324,246 | 4/1982 | Mullane et al. | 128/287 |
| 4,340,058 | 7/1982 | Pierce et al. | 128/287 |
| 4,342,314 | 8/1982 | Radel et al. | 128/287 |
| 4,433,972 | 2/1984 | Malfitano | 604/385 |
| 4,458,468 | 7/1984 | Silvilich | 53/428 |
| 4,463,045 | 7/1984 | Ahr et al. | 428/131 |
| 4,490,147 | 12/1984 | Pierce et al. | 604/378 |
| 4,501,586 | 2/1985 | Holtman | 604/380 |
| 4,526,825 | 7/1985 | Whitehead | 428/74 |

(List continued on next page.)

FOREIGN PATENT DOCUMENTS

| | | |
|---|---|---|
| 0400694A1 | 12/1990 | European Pat. Off. |
| 0534488A1 | 3/1993 | European Pat. Off. |
| 0597273A1 | 5/1994 | European Pat. Off. |
| 0607985A1 | 7/1994 | European Pat. Off. |
| 0626158A1 | 11/1994 | European Pat. Off. |
| 0626158 | 11/1994 | European Pat. Off. |
| WO93/01782 | 2/1993 | WIPO |
| WO93/12745 | 7/1993 | WIPO |
| WO93/19711 | 10/1993 | WIPO |
| WO94/16658 | 8/1994 | WIPO |
| WO94/27538 | 12/1994 | WIPO |

OTHER PUBLICATIONS

Concept Screen.

*Primary Examiner*—John G. Weiss
*Assistant Examiner*—David J. Cho
*Attorney, Agent, or Firm*—Mark L. Davis

[57] ABSTRACT

An absorbent article with an outer perimeter is disclosed having a cover, a baffle, an absorbent core and a barrier means for intercepting fluid migrating from the absorbent core toward the outer perimeter of the sanitary napkin. The absorbent core has a protuberance that extends above a plane that is parallel to the absorbent core periphery. The barrier can encircle the protuberance so that in use the barrier effectively forms a gasket between the wearer's body, such as the crotch and/or thighs and the absorbent article.

23 Claims, 2 Drawing Sheets

U.S. PATENT DOCUMENTS

| | | | |
|---|---|---|---|
| 4,554,191 | 11/1985 | Korpman | 428/35 |
| 4,559,051 | 12/1985 | Hanson | 604/385 R |
| 4,579,556 | 4/1986 | McFarland | 604/385 A |
| 4,624,666 | 11/1986 | DeRossett et al. | 604/366 |
| 4,631,062 | 12/1986 | Lassen et al. | 604/385 R |
| 4,648,876 | 3/1987 | Becker et al. | 604/370 |
| 4,655,759 | 4/1987 | Romans-Hess et al. | 604/385 R |
| 4,657,538 | 4/1987 | Becker et al. | 604/381 |
| 4,673,403 | 6/1987 | Lassen et al. | 604/385 R |
| 4,681,578 | 7/1987 | Anderson et al. | 604/385 R |
| 4,681,793 | 7/1987 | Linman et al. | 428/138 |
| 4,685,914 | 8/1987 | Holtman | 604/368 |
| 4,690,679 | 9/1987 | Mattingly, III et al. | 604/383 |
| 4,692,160 | 9/1987 | Nussbaumer | 604/331 |
| 4,701,177 | 10/1987 | Ellis et al. | 604/385 A |
| 4,710,185 | 12/1987 | Sneyd, Jr. et al. | 604/372 |
| 4,710,186 | 12/1987 | DeRossett et al. | 604/383 |
| 4,731,065 | 3/1988 | Yamada | 604/355 |
| 4,753,644 | 6/1988 | Cottenden et al. | 604/378 |
| 4,755,413 | 7/1988 | Morris | 428/138 |
| 4,758,240 | 7/1988 | Glassman | 604/379 |
| 4,770,657 | 9/1988 | Ellis et al. | 604/385 A |
| 4,772,282 | 9/1988 | Oakley | 604/385.1 |
| 4,781,713 | 11/1988 | Welch et al. | 604/385.1 |
| 4,795,454 | 1/1989 | Dragoo | 604/385.2 |
| 4,795,455 | 1/1989 | Luceri et al. | 604/386 |
| 4,798,603 | 1/1989 | Meyer et al. | 604/378 |
| 4,804,380 | 2/1989 | Lassen et al. | 604/385.1 |
| 4,808,177 | 2/1989 | DesMarais et al. | 604/385.1 |
| 4,828,555 | 5/1989 | Hermansson | 604/379 |
| 4,846,824 | 7/1989 | Lessen et al. | 604/385.1 |
| 4,865,597 | 9/1989 | Mason, Jr. et al. | 604/385.1 |
| 4,872,870 | 10/1989 | Jackson | 604/366 |
| 4,886,513 | 12/1989 | Mason, Jr. et al. | 604/385.1 |
| 4,908,026 | 3/1990 | Sukiennik et al. | 604/378 |
| 4,944,735 | 7/1990 | Mokry | 604/385.2 |
| 4,950,262 | 8/1990 | Takagi | 604/385.1 |
| 4,988,344 | 1/1991 | Reising et al. | 604/368 |
| 4,988,345 | 1/1991 | Reising | 604/368 |
| 5,013,309 | 5/1991 | Baigas, Jr. et al. | 604/368 |
| 5,021,051 | 6/1991 | Hiuke | 604/385.2 |
| 5,026,364 | 6/1991 | Robertson | 604/385.1 |
| 5,030,229 | 7/1991 | Yang | 604/385.1 |
| 5,032,121 | 7/1991 | Mokry | 604/385.2 |
| 5,037,409 | 8/1991 | Chen et al. | 604/358 |
| 5,053,029 | 10/1991 | Yang | 604/385.1 |
| 5,064,489 | 11/1991 | Ujimoto et al. | 156/164 |
| 5,074,855 | 12/1991 | Rosenbluth et al. | 604/385.1 |
| 5,074,856 | 12/1991 | Coe et al. | 604/385.1 |
| 5,092,860 | 3/1992 | Pigneul | 604/380 |
| 5,104,396 | 4/1992 | Oatley et al. | 604/379 |
| 5,129,893 | 7/1992 | Thoren | 604/385.2 |
| 5,134,007 | 7/1992 | Reising et al. | 428/78 |
| 5,135,521 | 8/1992 | Luceri et al. | 604/383 |
| 5,171,302 | 12/1992 | Buell | 604/385.1 |
| 5,181,563 | 1/1993 | Amaral | 604/385.2 |
| 5,197,959 | 3/1993 | Buell | 604/385.1 |
| 5,207,662 | 5/1993 | James | 604/385.2 |
| 5,211,641 | 5/1993 | Roos et al. | 604/385.1 |
| 5,219,341 | 6/1993 | Serbiak et al. | 604/361 |
| 5,234,422 | 8/1993 | Sneller et al. | 604/385.2 |
| 5,248,309 | 9/1993 | Serbiak et al. | 604/368 |
| 5,267,992 | 12/1993 | Van Tilburg | 604/387 |
| 5,275,591 | 1/1994 | Marvinkurve | 604/387 |
| 5,281,208 | 1/1994 | Thompson et al. | 604/378 |
| 5,324,278 | 6/1994 | Visscher et al. | 604/385.1 |
| 5,366,453 | 11/1994 | Zehner et al. | 604/385.1 |
| 5,382,245 | 1/1995 | Thompson et al. | 604/367 |

ABSORBENT ARTICLE HAVING BARRIER MEANS AND MEDIAL BULGE

FIELD OF THE INVENTION

This invention relates to an absorbent article for absorbing body fluid and in particular menstrual fluid. Particulary, this invention relates to sanitary napkins. More particularly, the present invention relates to sanitary napkins having a central absorbent protuberance for close body contact and barrier means for intercepting fluid migration. The barrier means effectively forms a gasket between the body of the wearer and the absorbent article, thus providing a comfortable and highly efficient catamenial device.

BACKGROUND OF THE INVENTION

All manner and variety of absorbent devices or appliances have been configured for the absorption of body fluids, such as menses, and are well known. Sanitary napkins are the most frequently used of these devices.

In the formation of such absorbent devices for the absorption of human exudate, the sanitary napkin commonly includes a liquid-permeable, bodyfacing cover, an absorbent core and a liquid-impermeable backing sheet or baffle. These absorbent devices, whether utilized as diapers, incontinence garments or sanitary napkins are subject to failure resulting in the movement of fluid across the face of the cover and/or through the absorbent core and leaking onto the wearer or the wearer's undergarment. In the area of sanitary napkins, it has been suggested that at least 20–25 percent of all sanitary napkins have side leakage. This incidence of leakage increases especially for those sanitary napkins having increased absorbency designed primarily for medium to heavy flow.

To overcome the problem of side leakage, sanitary napkins have been constructed having elasticized sides that urge the sides upward or cause the sanitary napkin to form a cup shape.

Another method of preventing side leakage has been to extend wings from the edges of the sanitary napkin. The wings generally extend over the edges of the undergarment crotch portion and adhere to the crotch portion or to themselves. The wings typically assist the garment adhesive, if present, to hold the sanitary napkin in position during use. However, it is possible that these elasticized edges or wings will fold inward, partially occluding the cover surface and thereby diminishing the efficacy of the sanitary napkin. In some cases this folding results in the edges actually contributing to incidence of failure.

Therefore, there remains a need for a sanitary napkin that will be comfortable to wear while decreasing the chance of side leakage associated with the use of sanitary napkins during the menstrual period.

SUMMARY OF THE INVENTION

Briefly, this invention relates to disposable absorbent articles, and more particularly to sanitary napkins which are designed to absorb body fluids, such as menstrual fluid, and other excrements discharged by the body during a menstrual period. The present invention provides for an absorbent article having close body contact and improved side leakage protection. Although described hereafter as a sanitary napkin, it is understood that the invention can be adapted for use in disposable diapers, adult incontinence devices and the like where absorption of at least 8 grams of fluid is desired.

The sanitary napkin generally includes a liquid-permeable cover, a liquid-impermeable baffle and an absorbent core located between the cover and the baffle. In one embodiment, the cover and baffle extend beyond the absorbent core to define an outer perimeter of the sanitary napkin. The absorbent core has a periphery inward from the outer perimeter. In another embodiment, the cover envelopes the absorbent core and is secured to itself on the garment facing side. In this embodiment, the outer perimeter of the sanitary napkin is coincident with the periphery of the absorbent core. The baffle is then secured to the cover on the garment facing side. For both of the above embodiments the absorbent core includes an absorbent protuberance that projects above a plane residing parallel to the periphery of the absorbent core.

In a preferred embodiment, the protuberance is longitudinally oriented. The protuberance is preferably formed from a wet stable absorbent material having a density, relatively speaking, less than or equal to the absorbent located adjacent to the baffle.

The sanitary napkin further includes a barrier positioned between an edge of the absorbent protuberance and the perimeter of the sanitary napkin. The barrier impedes and preferably intercepts the flow of body fluid that may migrate toward the perimeter of the sanitary napkin. The height of the barrier should be at least equal to the thickness of the absorbent located at the periphery of the absorbent core.

It is a primary object of this invention to provide an absorbent article exhibiting improved body contact as well as improved side leakage protection, that is, preventing fluid run-off beyond the perimeter of the absorbent article.

It is another object of this invention to provide an improved sanitary napkin having a protuberance and a fluid barrier. The protuberance improves the body contact of the sanitary napkin and the fluid barrier forms an effective gasket between the body of the wearer and the sanitary napkin to thereby improve the overall efficacy of the sanitary napkin.

Another object of this invention is to provide a sanitary napkin which is absorbent enough for medium to heavy menstrual flows and provides intimate contact to the wearer's body, improved side leakage prevention and is comfortable to wear.

These and other objects, features and advantages are readily apparent when considered in reference to the following specification and the accompanying drawings, wherein there are illustrated and described sanitary napkins showing preferred embodiments of the present invention. In the Figures, like parts and objects in the various views have similar reference numerals with the different embodiments differentiated by the use of a prime or double prime suffix. It is to be understood that the inventive concept is not to be considered limited to the constructions disclosed except as determined by the scope of the appended claims.

DETAILED DESCRIPTION OF THE PREFERRED EMBODIMENTS

Figure 1:
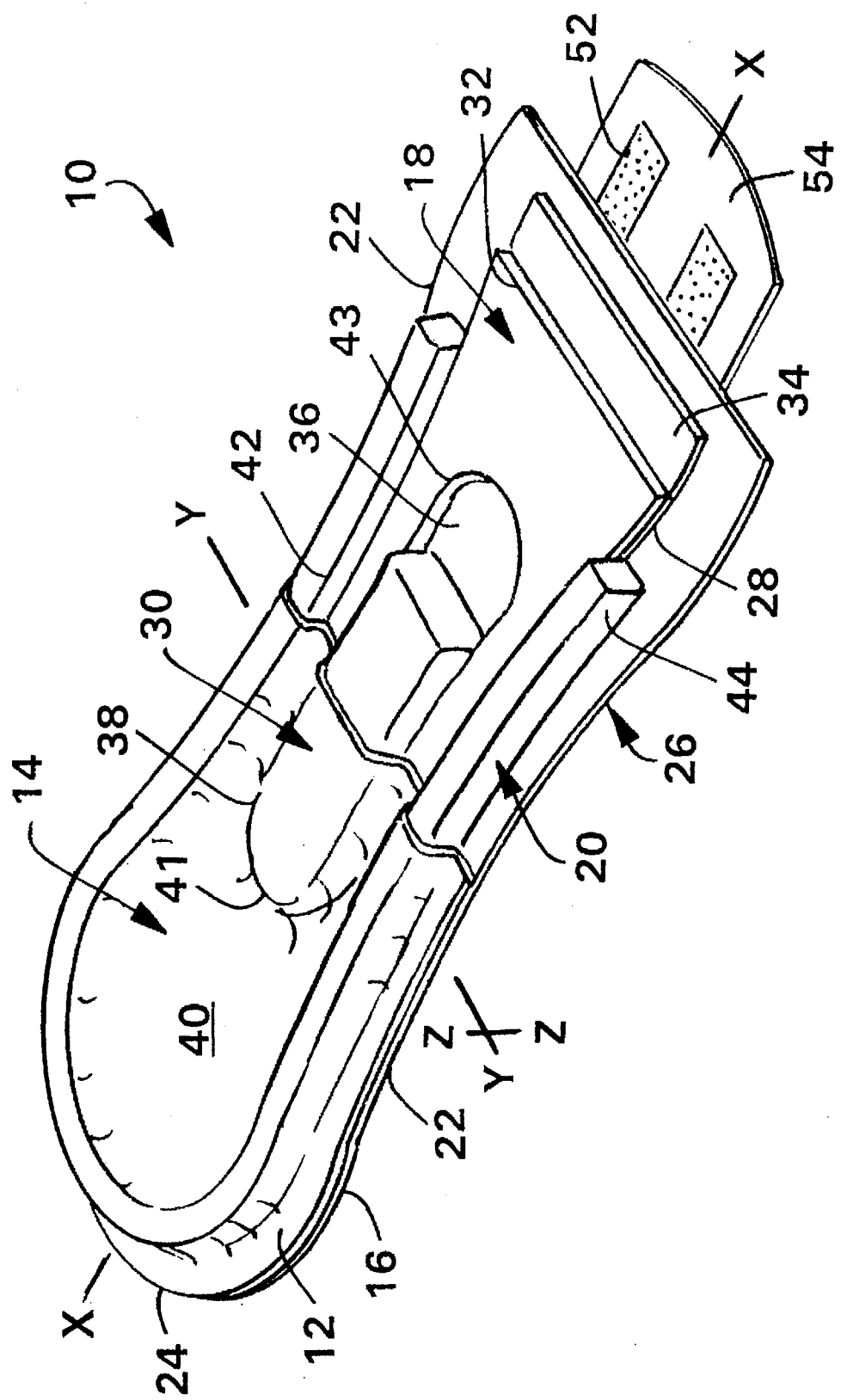
FIG. 1 is a partial cutaway of a perspective view of an absorbent article, illustrated as a sanitary napkin, showing a generalized construction and an embodiment of the present invention.

Referring to FIG. 1, an absorbent article 10 is illustrated in the form of a sanitary napkin. Typically, the sanitary napkin 10 is worn by a female to absorb body fluids, such as menses, blood, urine and other body excrements discharged during a menstrual period. Although the present invention will be described with reference to a sanitary napkin 10, those skilled in the art will realize that such description is meant to be exemplary only and should not be deemed as limiting the scope of the present invention. The present invention will now be described in greater detail with reference to the Figures.

The sanitary napkin 10 includes a liquid-permeable cover 12 having a bodyfacing surface 14, a liquid-impermeable, garment facing baffle 16, an absorbent core 18 intermediate the cover 12 and the baffle 16 and a barrier device 20 positioned adjacent to the absorbent core 18. The sanitary napkin 10 has a pair of spaced apart longitudinal edges 22 and transverse ends 24, only one of which is shown in FIG. 1. The longitudinal edges 22 and transverse ends 24 collectively form the perimeter 26 of the sanitary napkin 10. The sanitary napkin 10 is about 150 millimeters (mm) to about 300 mm long and about 50 mm to about 175 mm wide at its widest point. The sanitary napkin 10 has an hourglass configuration but can include such shapes as rectangular, oval, racetrack, dogbone and the like. The sanitary napkin should have a caliper of less than about 15 mm but will preferably range from a few millimeters to about 15 mm depending upon the location of the measurement reading as explained in greater detail below.

As is customary in the art, the cover 12 is fluid pervious and is adapted to reside on that side of the sanitary napkin 10 to be in contact with the body of the wearer. The cover 12 can be a resilient, relatively non-absorbing fluid pervious material. The cover 12 is provided for comfort and conformability and functions to direct fluid to the underlying absorbent core 18 which retains such fluid. The cover 12 can be constructed of any woven or nonwoven material which is easily penetrated by body fluid contacting its surface. Preferably, the cover 12 is made of a material which allows the passage of fluid without wicking it appreciably in a horizontal plane parallel to the cover 12. Furthermore, the cover 12 should retain little or no fluid in its structure so that it provides a relatively dry surface next to the skin. Generally, the cover 12 is a single, rectangular sheet of material having a width sufficient to overlie the bodyfacing side of the absorbent core 18. The cover 12 can be constructed of bonded carded webs of polyester, polypropylene, polyethylene, nylon, or other heat-bondable fibers. Other polyolefins, such as copolymers of polypropylene and polyethylene, liner low-density polyethylene, finely perforated film webs and net material also work well. Other suitable materials are composite materials of polymer and a nonwoven fabric material. The composite sheets are generally formed by extrusion of polymer onto a web of spunbond material to form an integral sheet. This material is preferred because the outer fabric surface is not irritating to the skin of the wearer and has a cushion feel.

Another preferred material for the cover 12 is a spunbond web of polypropylene. The web can contain about 1 to 6 percent titanium dioxide pigment to give it a clean white appearance. A uniform spunbond material is desirable because it has sufficient strength, after being perforated in the longitudinal direction, to resist being torn or pulled apart during use. The most preferred polypropylene webs have a weight of between about 18 and 40 grams per square meter. Desirably, the weight is between about 30 and about 40 grams per square meter.

The liquid-permeable cover 12 can also contain a plurality of apertures (not shown) formed therein. Such apertures can be arranged along a longitudinal central axis X—X if desired, and are intended to increase the rate at which body fluids can penetrate down into the first absorbent layer 12.

With apertures present, body fluid, which is deposited at or near the apertures, rapidly migrates into the absorbent core 18. This helps maintain a perceivably drier surface than when the apertures are not present. Therefore, while the apertures are not essential, a functional advantage is obtained by their use.

The liquid-permeable cover 12 can also be treated with a surfactant to make it more hydrophilic and, thereby, aid in the absorption of the liquid. The surfactant can include topical additions or internally applied materials like polysiloxanes.

As indicated, the liquid-impermeable baffle 16 is coextensive with the liquid-permeable cover 12 and is adhered to the cover 12 in those areas where the cover 12 and the baffle 16 are in face-to-face contact. One will also understand that it may be advantageous for liquid transfer from the cover 12 to the absorbent core 18 that the cover 12 be secured to the absorbent core 18. The method of adhering the cover 12 to the baffle 16, and if so desired the absorbent core 18, may be any suitable method that does not leave a hard, uncomfortable residue that would be annoying to the wearer. Methods for joining the various materials are well known to those skilled in the art and include the use of hot melt adhesives in a uniform and continuous or non-continuous layer, patterned adhesives, pressure sensitive adhesives, double-sided tape, sonic bonding, and heat sealing to name a few.

Referring to FIG. 1, the absorbent core 18 has, generally, a periphery 28 located inward from the perimeter 26 of the sanitary napkin 10 so that the cover 12 and the baffle 16, in combination, will enclose the absorbent core 18. The absorbent core 18 provides the means for absorbing the menstrual fluid. The total absorbent capacity of the absorbent core 18 should be compatible with the design exudate loading in the intended use of the sanitary napkin 10 but preferably is adapted to absorb fluid from a woman having a medium to heavy flow. Generally, the amount of menses representative of this type of flow is greater than about 5 grams. Further, the size and shape of the absorbent core can be varied. For example, the absorbent core 18 can be rectangular, oval or racetrack. Preferably, the absorbent core 18 has an hourglass configuration.

The absorbent core 18 is generally made from material(s) that are hydrophilic, compressible, conformable and non-irritating to the wearer's skin. Acceptable materials are well known in the art and include, for example, various natural or synthetic fibers, wood pulp fibers, regenerated cellulose or cotton fibers, or a blend of pulp and other fibers, meltblown polymer, such as polyester, and polypropylene. The absorbent layers may also be comprised of other well-known materials used in absorbent articles, including multiple layers of cellulose wadding, rayon fibers, cellulose sponge, hydrophilic synthetic sponge, such as polyurethane, and the like.

In the preferred embodiments of the sanitary napkin 10 illustrated in FIGS. 1–4, the absorbent core 18 is a composite of absorbent materials. The upper most surface of the absorbent core 18, i.e., the side of the absorbent disposed toward the cover 12, includes an absorbent protuberance or first layer 30. Preferably, absorbent material used to form the protuberance 30 is less dense relative to the absorbent material proximate the baffle 16. It has been found that by providing the absorbent core 18 with a low-to-high density gradient, as viewed from the cover 12 to the baffle 16, a capillary action is produced that draws the fluid into the absorbent core 18 and away from the cover 12. The density of the absorbent material forming the protuberance 30 should be such that the protuberance 30 will readily conform to the anatomical differences of the individual and provide contact to the body without becoming intrusive to the wearer. That is, the protuberance 30 preferably will conform to the anatomical shape of the wearer defined by the inwardly-facing surfaces of the wearer's labia majora without feeling intrusive.

Generally, the absorbent material used in forming the protuberance 30 has an insufficient absorbent capacity for the sanitary napkin but should provide good wicking properties in the Z-direction. The term "Z-direction" means a direction that is associated with the thickness of the sanitary napkin 10, as is shown in FIG. 1, and is perpendicular to the plane established by the X and Y directions. Absorbency in the Z-direction is important because a primary purpose of the protuberance 30 is to acquire and distribute liquid to the absorbent core 18 which has passed through the cover 12.

Figure 2:
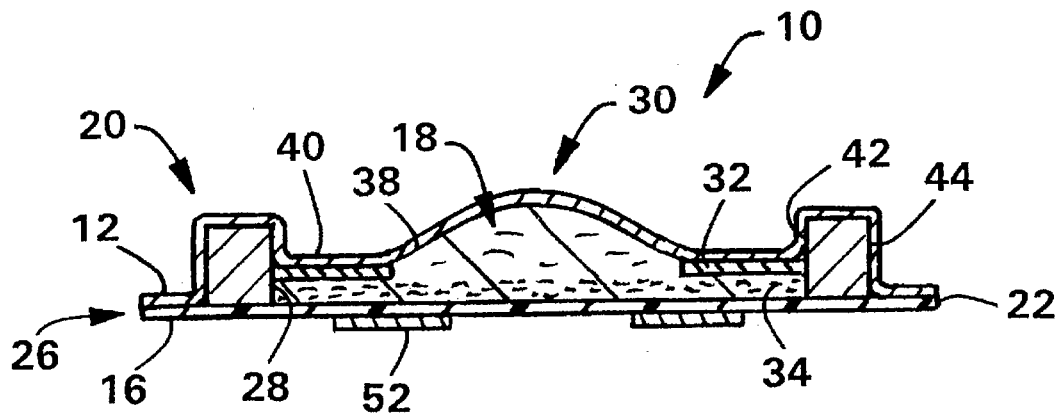
FIG. 2 is a cross-sectional view of the sanitary napkin taken along line Y—Y of FIG. 1

Referring to FIGS. 1 and 2, the absorbent core 18 includes a second layer 32 positioned between the cover 12 and the baffle 16 and is adjacent to the absorbent of the protuberance 30. The second absorbent layer 32 can have a fluid wicking capacity greater than or equal to the fluid wicking capacity of the absorbent comprising the protuberance 30. Suitable materials include, for example, coform, meltblown and tissue. Coform is a meltblown air-formed combination of meltblown polymers, such as polypropylene, and absorbent staple fibers, such as cellulose.

In a preferred embodiment, the absorbent core 18 includes a third absorbent layer 34 positioned between the second layer 32 and the baffle 16. It is desirable for the second layer 32 and/or the third layer 34 to be wet stable as this helps the absorbent core 18 to retain its shape after becoming insulted with the body fluid. The term "wet stable" means that the fibers of the layer, when wetted, do not clump together or substantially lose their ability to retain or return to their non-wetted configuration. Examples of such materials include a meltblown polypropylene. Other materials may also be used in conjunction with one or more of the above absorbent materials to render the layer as a whole "wet stable."

The absorbent layers 32 and 34 may contain superabsorbent particles which are effective in retaining body fluids. Superabsorbents have the ability to absorb a large amount of fluid in relation to their own weight. Typical superabsorbents used in absorbent articles, such as sanitary napkins, can absorb anywhere from 5 to 60 times their weight in body fluids. However, the absorption mechanism of the superabsorbents is usually slower than the rate of fluid absorption by cellulose fluff material. The placement of the superabsorbent particles is not critical but have been found to be effective when placed in the central portion of the sanitary napkin 10 as this provides additional time for the superabsorbent particles to absorb the body fluid.

Referring to FIG. 1, the second absorbent layer 32 includes an aperture 36, which preferably is coaxially aligned with the protuberance 30. The aperture 36 can be of any size to adequately allow for liquid communication between the protuberance 30 and the third layer 34. The aperture 36 can be a single opening or a plurality of apertures 36 which collectively have a sufficient open area to allow for liquid communication between the absorbent layers. Preferably, the aperture 36 will be of a dimension less than or equal to the width of the protuberance 30. The aperture 36 provides a means for the third absorbent layer 34 to rapidly desorb the absorbed fluid present in the protuberance 30. Thus, this multilayer absorbent configuration provides a highly effective absorbent core for fluid absorption.

The protuberance 30 generally extends above a plane that is parallel to the periphery 28 of the absorbent core 18, preferably is longitudinally oriented and more preferably longitudinally oriented and medially centered along the longitudinal central axis X—X of the sanitary napkin 10. The term "median" or "medial" is used herein to mean that the transverse ends of the protuberance 30 are equidistant from the transverse ends 24 of the sanitary napkin 10. Accordingly, the protuberance 30 does not have to be centered relative to the longitudinal edges 22 of the sanitary napkin 10, but it is preferred that the longitudinal axis X—X of the sanitary napkin 10 coincide with the longitudinal centerline of the protuberance 30.

The protuberance 30 has an edge 38 located where the elevation of the cover 12 changes due to the presence of the protuberance 30. When the aperture 36 is coaxially aligned with the protuberance 30 and has a width equal to the width of the protuberance 30, the edge 38 substantially coincides with the lateral dimensions of the aperture 36.

Flanking the edge 38 is a planar region 40. The planar region 40 extends from the edge 38 to the periphery 28 of the absorbent core 18. The absorbent in the planar region 40 generally has the bulk of the absorbent capacity of the sanitary napkin 10.

The protuberance 30 is three-dimensional having a length, a width and a height. The protuberance 30 can be any shape provided that it at least contacts a portion of the labia majora of the wearer. The overall shape of the protuberance 30 can be asymmetrical but symmetry is preferred. Nonlimiting examples of suitable shapes for the protuberance 30 include oval, rectangular, square, i.e. box shaped, semi-cylindrical, i.e. cylindrical having a plane passing longitudinally from one end to the other, and semi-spherical, i.e., dome shaped. It is to be understood that the term "height" is used interchangeably herein with thickness. The length of the protuberance 30 is measured longitudinally from one transverse edge 41 to the other transverse edge 43. The width is generally measured transversely from one longitudinal edge of the protuberance 30 to the other longitudinal edge. That is, the width is measured along a co-planar line Y—Y which runs perpendicular to the longitudinal axis X—X. The height is the perpendicular distance from a plane parallel to the periphery 28 of the absorbent core 18 to the upper most top surface or apex of the cover 12. This point is typically located along the longitudinal centerline of the protuberance 30. It is to be understood that the height of the protuberance 30 is different from the caliper of the sanitary napkin 10. The caliper typically will be used to express the entire thickness of the sanitary napkin 10 at the apex of the protuberance 30. The length of the protuberance 30 can range from between about 1.5 centimeters (cm) to the length of the absorbent core 18, preferably about 2 cm to about 12 cm, and more preferably, from about 4 cm to about 8 cm. The width of the protuberance 30 can vary from about 1 cm to about 5 cm, preferably from about 1.5 cm to about 4 cm and most preferably, from about 1.5 cm to about 3 cm. The height of the protuberance 30 is preferably greater than twice the thickness of the surrounding planar region 40, more preferably, from about 3 millimeters (mm) to about 25 mm, still more preferably, from about 3 mm to about 20 mm and most preferably, from about 5 mm to about 15 mm. A convenient method of measuring the height of the protuberance 30 is to measure the caliper at the apex of the protuberance 30 and subtract the caliper of the surrounding planar region 40.

The exterior dimensions of the protuberance 30, other than the caliper, are measured using a standard ruler without any load being placed on the product.

The caliper of the sanitary napkin 10 can be measured in accordance with the following procedure. All measurements are made on newly unpacked absorbent products. Each napkin should be removed from its package for at least 30 minutes and handled carefully to avoid compressing, or otherwise affecting the properties thereof. Unless otherwise stated, all tests are performed at a relative humidity of 50%±2% and a temperature of 73° F. and with any peel strip removed and the adhesive blocked using talc or corn starch.

It is the planar region 40 that is of interest, rather than any other portion of the sanitary napkin 10 that lies laterally outboard thereof (an example of these latter parts are where the cover 12 and baffle 16 extend into a seal around the perimeter 26 of the sanitary napkin 10) which do not contain significant absorbent material but which may be more flexible and have calipers less than the calipers of the planar region 40.

The caliper of a sanitary napkin 10, or various regions thereof, is determined by the following test. At least one measurement is taken in the longitudinal central region of the sanitary napkin 10 at the point of maximum height of the protuberance 30. At least one measurement is taken in the surrounding planar region 40 of the sanitary napkin 10. For the purposes of this measurement the barrier 20 is not included.

A comparator gauge, (Ames, Model 130 with a dial indicator Model 482, available from the B.C. Ames, Company of Waltham, Mass.) is needed. The comparator gauge should typically have a circular comparator foot made of aluminum and a weight of 10.0 grams and a contact surface of 5.16 square centimeters. The gauge is provided with an 80.0 gram stainless steel weight to provide a total of 0.25 psi pressure. If due to the shape of the region to be tested, it is not possible to use a circular comparator foot and achieve an accurate measurement of the region, a 1"×¼" rectangular comparator foot should be used and a test weight should be used that provides a total pressure of 0.25 psi. The comparator gauge is first zeroed. The weight is then placed on the spindle extending above the comparator dial. The release paper is removed and the garment adhesive, if any, is blocked using corn starch. The comparator foot is then raised and the napkin is placed on the base plate, garment surface down. The napkin is positioned on the base plate so that when the foot is lowered it is in the region of the napkin for which the measurement is desired. The sanitary napkin 10 should have as few a wrinkles as possible before testing. Gently lower the foot onto the napkin. Determine the napkin caliper by reading the comparator dial 30 seconds after the foot comes in contact with the napkin.

The surrounding planar region 40 can have a caliper of less than or equal to about 10 millimeters, preferably less than or equal to about 7 millimeters, and more preferably, less than or equal to about 3 millimeters.

The caliper of the central longitudinal region incorporating the protuberance 30, of course, will typically be greater than the calipers specified above. The calipers of the various alternative embodiments of the sanitary napkin 10 as measured along the principal longitudinal centerline X—X are set out above.

The flexibility of the various regions of the sanitary napkin 10 is expressed in terms of flexure-resistance. The flexibility is measured according to the Circular Bend Procedure (described in greater detail below). The longitudinal central region incorporating the protuberance 30 has a flexure-resistance of less than or equal to about 1,000 grams, preferably less than to about 700 grams and most preferably, less about 600 grams.

The surrounding planar region 40 has a flexure resistance less than or equal to that of the longitudinal central region incorporating the protuberance 30. Desirably, the flexure resistance is less than about 900 grams, more preferably, less than about 700 grams, most preferably, less than about 500 grams.

The flexure-resistance of the different regions of the sanitary napkin 10 is measured as peak bending stiffness. Peak bending stiffness is determined by a test which is modeled after the ASTM D4032-82 Circular Bend Procedure. This modified test is used for the purposes of the present invention and is, hereinafter, simply referred to as the "Circular Bend Procedure". The Circular Bend Procedure is a simultaneous multi-directional deformation of a material in which one face of a specimen becomes concave and the other face becomes convex. The Circular Bend Procedure gives a force value related to flexure-resistance, simultaneously averaging stiffness in all directions.

In the case of the present invention when carrying out the Circular Bend Procedure, separate samples of the sanitary napkins are taken along the longitudinal central axis X—X, from the surrounding planar region 40 and from an area that would include a portion of the barrier 20 with the planar region 40. The samples are tested and averaged separately so a flexure-resistance value is obtained for the longitudinal central region, and a separate value is obtained for the surrounding planar region 40.

The apparatus necessary for the Circular Bend Procedure is a modified Circular Bend Stiffness Tester, having the following parts: A smooth-polished steel plate platform which is 102.0×102.0×6.35 millimeters having an 18.75 millimeter diameter orifice. The lap edge of the orifice should be at a 45 degree angle to a depth of 4.75 millimeters. A plunger having the following dimensions: overall length of 72.2 millimeters, a diameter of 6.25 millimeters, a ball nose having a radius of 2.97 millimeters and a needle-point extending 0.88 millimeters therefrom with a 0.33 millimeter base diameter and a point having a radius of less than 0.5 millimeters is used for the test. The plunger is mounted concentrically with the orifice having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to the exact bottom of the plate orifice.

A force measurement gauge is also needed. An Instron inverted compression load cell having a load range of from about 0.0 to about 2000.0 grams works fine.

An actuator, and more specifically the Instron Model No. 1122 having an inverted compression load cell. The Instron 1122 is made by the Instron Engineering Corporation of Canton, Mass.

In order to perform the procedure for this test, as explained below, five representative sanitary napkins are necessary. From one of the five napkins to be tested, some number "Y" of 37.5×37.5 millimeter test specimens are cut. At least one specimen is cut from the portion of the sanitary napkin containing the point of maximum amplitude of the protuberance 30 thereon, and at least one specimen is cut from the surrounding planar region 40 of the sanitary napkin 10. If due to the shape of the region to be tested, it is not possible to cut a square 37.5×37.5 millimeter specimen, any other 1,400 square millimeter size specimen may be used, provided the specimen adequately covers the orifice in the test platform to properly carry out the test.

Specimens having portions in which a cover 12 is joined directly to a baffle 16 or which are a laminate of a cover 12, two or less tissue sheets and a baffle 16, should also not be tested. The reason that these specimens are not tested is due to the realization that prior art napkins exist in which a cover 12 is joined to a barrier sheet beyond the edges of an absorbent core in the periphery of the napkin, such portions of which are highly flexible. The present invention is more concerned with the flexibility of the significant absorbent portions of the sanitary napkin. The term "significant absorbent portions," as used herein, refers to those portions in the main body portion of the sanitary napkin 10 that contain absorbent material. A number of different specimens should be tested from each sanitary napkin. In particular, the structurally least flexible portions in the center of the sanitary napkin should be tested as the longitudinal central region. The most flexible portions of the sanitary napkin should be tested when samples of the surrounding regions of the napkin are measured.

The test specimens should not be folded, bent or compressed by the test person, and the handling of specimens must be kept to a minimum and to the edges to avoid affecting flexural-resistance properties. From the four remaining sanitary napkins, an equal number "Y" of specimens, identical to the specimens cut from the first napkin, are cut. Thus, the test person should have "Y" number of sets of five identical specimens.

The procedure for the Circular Bend Procedure is as follows. The specimens are conditioned by leaving them in a room which is 21°±1° C. and 50±2% Relative Humidity for a period of at least two hours. The test plate is leveled. The plunger speed is sets at 50.0 centimeters per minute per full stroke length. A specimen is centered on the orifice platform below the plunger such that the cover 12 of the specimen is facing the plunger and the baffle 16 of the specimen is facing the platform with the release paper removed from any adhesive on the garment surface of the specimen and the adhesive sprinkled with corn starch, talc or any other suitable composition that will to eliminate the adhesive tack. The indicator zero is checked and adjusted, if necessary. The plunger is actuated. Touching the specimen during the test should be avoided. The maximum force reading to the nearest gram is recorded. The above steps are repeated until all five of the identical specimens have been tested.

The peak bending stiffness for each specimen is the maximum force reading for that specimen. Each set of five identical specimens is tested and the five values received for that set are averaged. Thus, the test person now has an average value for each of the "Y" identical sets of specimens tested. If any of the significant absorbent portions of the sanitary napkin have the requisite flexure-resistances, then the napkin satisfies the parameters of this test.

The sanitary napkin 10 has a liquid capacity great enough to absorb medium to high menstrual flows. The capacity of the sanitary napkin 10 is defined in terms of two capacities, which, depending on the size of the sanitary napkin may be the same: test capacity and total capacity.

The sanitary napkin 10 should have a test capacity of at least about 5.0 grams, more preferably at least about 10.0 grams, more preferably at least about 15.0 grams, and most preferably at least about 18.0 grams. The sanitary napkin 10 should have a total capacity of at least about 10.0 grams, preferably at least about 15.0 grams, and more preferably at least about 20.0 grams.

The test and total capacities of a sanitary napkin are determined as follows. Any panty adhesive release paper is removed from the napkin to be tested. To determine test capacity, a sample is obtained from a 4.75×14.0 centimeter portion, or any other configuration having 66.5 square centimeters, of the sanitary napkin. The sample is cut from the portion of the sanitary napkin which would be centered under the vaginal orifice when the sanitary napkin is worn. Total capacity is determined using a sample comprising the entire napkin minus any release paper.

The sample is weighed to the nearest 0.1 gram. The sample is then submerged in a beaker of sterile saline (obtainable from the Baxter Travenol Company of Deerfield, Ill.), such that the sample is totally submerged and is not bent or otherwise twisted or folded. The sample is submerged for 10 minutes. The sample is removed from the saline and suspended for two minutes in a vertical position to allow the saline to drain out of the sample. The sample is then placed bodyfacing surface down onto an absorbent blotter, such as the filter paper #631 available from the Filtration Science Corp., Eaton-Dikeman Division of Mount Holly Springs, Pa. A uniform 17.6 gram per square centimeter load is placed over the sample to squeeze excess fluid out. The absorbent blotter is replaced every 30 seconds until the amount of fluid transferred to the absorbent blotter is less than 0.5 grams in a 30 second period. Next, the sample is weighed to the nearest 0.1 grams and the dry weight of the sample is subtracted. The difference in grams is the test or total capacity of the sample, whichever the case may be.

The barrier 20 has a pair of spaced apart lateral faces; an inner surface 42 and an outer surface 44. The inner surface 42 is disposed inwardly toward the protuberance 30 and the outer surface 44 is disposed outwardly away from the protuberance 30. The barrier 20 encircles the protuberance 30 and preferably, the absorbent core 18. By "encircles" we mean that the barrier 20 substantially forms a closed loop. One skilled in the art will understand that there may be small openings or gaps in the barrier 20 without jeopardizing the efficacy of the barrier 20 to intercept fluid migrating toward the perimeter 26 of the sanitary napkin 10. The invention described herein is intended to cover such modifications to the extent that an opening or gap does not exceed 2 centimeters.

The barrier 20 can encircle any portion of the absorbent core 18 but should not reside on the protuberance 30, however the inner surface 42 of the barrier 20 can be aligned with the edge 38 of the protuberance 30. Preferably the barrier 20 is positioned between the edge 38 and the perimeter 26 of the sanitary napkin 10, more preferably, between the periphery 28 and the perimeter 26 of the sanitary napkin 10, more preferably the outer surface 44 is coterminous with the perimeter 26 of the sanitary napkin 10 and especially preferred the inner surface 42 is adjacent to the periphery 28 of the absorbent core 18 so that the barrier effectively delimits the absorbent core 18. It is to be understood that the barrier 20 can be any combination of the above configurations. For example, it is possible that when the absorbent core 18 is in the shape of an hourglass, dogbone or any asymmetrical shape that the barrier 20 can reside adjacent to the periphery 28 at the widest portions of the absorbent core 18 and be positioned between the periphery 28 and the perimeter 26 at the narrower locations.

The barrier 20 can reside on top of the cover 12 or between the cover 12 and the baffle 16. Since the barrier 20 will preferably be in contact with the body of the wearer, so as to form a gasket between the wearer and the sanitary napkin 10, it is advantageous for the barrier 20 to be covered by a material that is soft and compliant, such as the cover 12. It is therefore preferred that the barrier 20 reside below the cover 12 and more preferred in contact therewith.

An advantage of the sanitary napkin 10 utilizing a protuberance 30 of the above-described characteristics and incorporating a barrier 20 is that the protuberance 30 can be less dense, i.e., loftier. This provides for a sanitary napkin 10 that is less intrusive to the wearer than sanitary napkins here-to-fore known or used that incorporate a hump, an extension or an elevated surface.

Another advantage of the present invention is a greater utilization of the absorbent material is realized. By impeding the flow of any body fluid toward the perimeter 26, additional time is permitted for the absorbent core 18 to absorb the body fluid.

The barrier 20 is desirably constructed of a flexible, easily compressible, resilient material and is preferably hydrophobic. The preferred materials for forming the barrier 20 are hydrophobic liquid-impermeable polymer foams, such as, for example polyurethane foams. Although hydrophobic polyurethane foams are a preferred material for constructing the barrier 20, other flexible, resilient materials may be employed such as those formed of foamed styrene butadiene, foamed polyethylene, foamed silicones, foamed vinyl plastics, soft sponge rubber and the like. Such foams can be obtained from Woodbridge Foam Fabricating, Inc., located at 1120 Judd Road, Chattanooga Tenn., from the E. N. Murray Company, Inc., having offices in Denver, Colo. and Astro-Valcour, INC., having offices at 18 Peck Ave., Glens Falls, N.Y.

The barrier 20 can also be hydrophilic or partially hydrophilic. A suitable hydrophilic material for use as a barrier 20 is a compressed cellulosic sponge. The cellulosic sponge should have a pore size sufficient for absorbing the intended body fluid. For example, in the case where menses is intended to be absorbed the pores of the sponge would be larger than if a less viscous liquid, such as urine, was the intended substance to be absorbed. In a preferred embodiment the cellulosic sponge is compressed to about 50% of its original height before incorporating the cellulosic sponge into the product and more preferably it is compressed to about 25% of its original height before incorporating into the product. Since the compressed cellulosic sponge has narrower capillary radii in its compressed state than its uncompressed state it is capable of rapid absorption of body fluids. Once wet, the cellulosic sponge barrier 20 expands and recovers to its uncompressed dimension. When the compressed cellulosic sponge is only partially wet, the interface between the wet and dry parts provides a junction area having wide and narrow capillaries. The narrow capillaries draw liquid from the wider capillaries, diffusing the body fluid from the wet part to the dry, compressed cellulosic sponge. This advantageously utilizes a greater amount of the available absorbent capacity of the absorbent core 18 by rapidly diffusing the fluid to those areas of the absorbent core 18 that have not yet been insulted with the body fluid. Using a compressed cellulosic sponge is advantageous because the sponge will expand to its uncompressed dimension when wetted which allows the barrier 20 to bulk up in those areas where fluid flow is migrating toward the perimeter. This also provides a better gasketing effect between the body of the wearer, such as the crotch or thigh regions of the wearer, and the sanitary napkin in those specific insulted areas.

It is important for wearer comfort and sealing purposes that the barrier 20 be soft, resilient and easily compressible. The resiliency should be in the range of about 15 percent to about 60 percent rebound, preferably about 15 percent to about 50 percent and more preferably about 15 percent to about 35 percent. Resiliency is determined by the ASTM Test Method D3574-91 procedure H. Compressibility should be in the range of about 0.1 psi to about 2 psi at 50% compression, preferably from about 0.3 psi to about 1.7 psi and most preferably from about 0.5 psi to about 1.5 psi. Compressibility is determined by the ASTM Test Method D3574-91 procedure C. Desirably, the foamed polymeric material will have a density of about 0.02 grams per cubic centimeter ($cm^3$) to about 0.1 grams per $cm^3$.

The barrier 20 should have a width ranging from about 3 mm to about 12 mm and a height of about 2 mm to about to about 25 mm; preferably, the width is from about 3 mm to about 8 mm and the height is from about 6 mm to about 15 mm; and most preferably, the width and the height are equal and range from about 4 mm to about 8 mm. The height of the barrier 20 should be sufficient to permit adaptation of the barrier 20 to changes in the surface contour. Such changes are generally attributed to the variable placements of the sanitary napkin 10 in the undergarment and the general physiology differences of the individual wearer. The barrier 20 should have a height at least equal to the thickness of the periphery 28 of the absorbent core 18.

Figure 3:
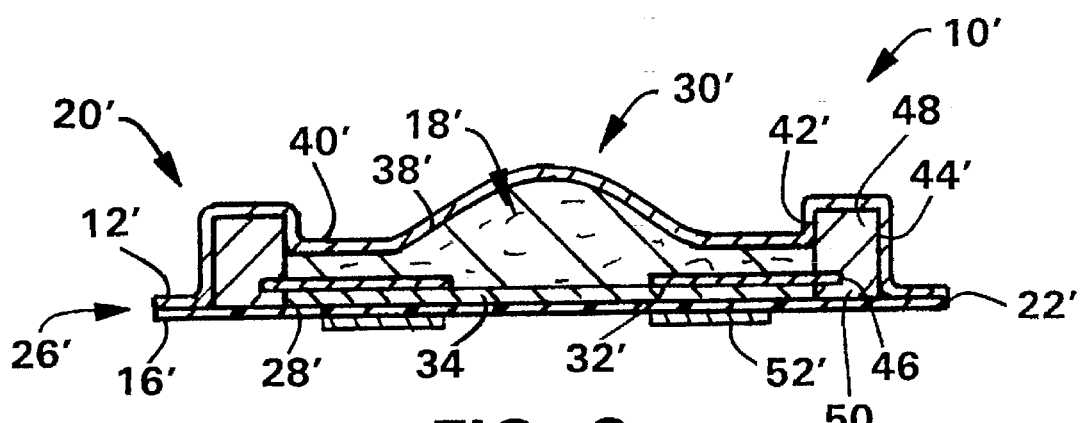
FIG. 3 is a cross-sectional view of another embodiment of the invention taken along a line similar to Y—Y shown in FIG. 1. The barrier device includes a channel partially dividing the barrier and having a portion of the absorbent inserted therein.
Figure 4:
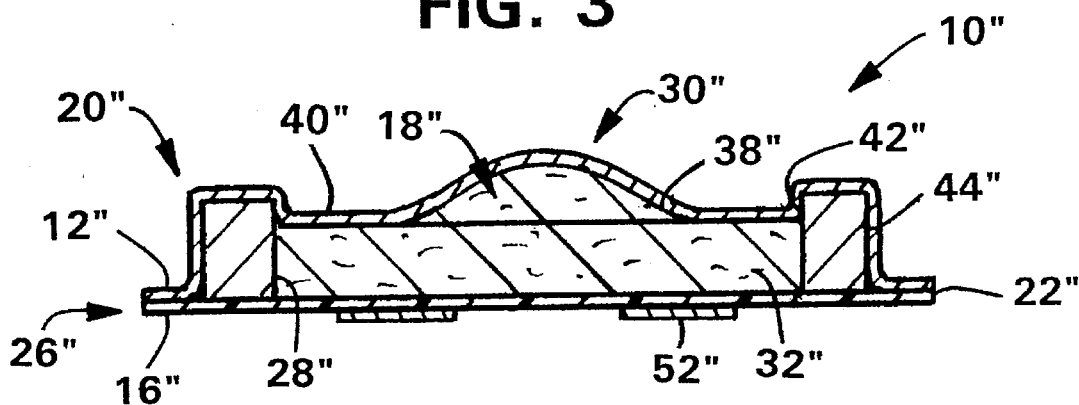
FIG. 4 is a cross-sectional view of another embodiment of the invention taken along a line similar to Y—Y shown in FIG. 1.

The construction of the sanitary napkin 10 may take various alternative embodiments such as illustrated, for example in the cross-sectional views shown in FIGS. 3–5. In FIG. 3 the materials and the construction of the sanitary napkin 10' are similar to that described above except for the following. The absorbent core 18' is constructed so that the absorbent material comprising the protuberance 30' extends from the edge 38' to the barrier 20'. The inner barrier surface 42' is at least partially segmented to provide a horizontal channel, groove or slit 46, (hereinafter channel 46). The channel 46 partially divides the barrier 20' into a top section 48 and a bottom section 50. The second layer of absorbent 32' is positioned so that it at least partially resides inside the channel 46 between the top and bottom sections 48 and 50. This allows the second layer 32' to be constructed from a lower density absorbent material than described above for FIGS. 1 and 2. The absorbent material can have a density ranging from about 0.05 grams per cubic centimeter (g/cc) to about 0.4 g/cc, preferably from about 0.05 g/cc to about 0.25 g/cc and more preferably 0.05 g/cc to about 0.12 g/cc.

In FIG. 4 a still different construction is shown and differs primarily from the construction of FIGS. 1–3 in that the absorbent core 18" is comprised of only one absorbent material. Although the protuberance 30" is similar to that described above, the second layer 32" has a greater density and absorbent capacity. In this embodiment, to prevent the body fluid from possibly pooling at or near the point of insult with the body fluid, the barrier 20" should extend above the plane of the surrounding planar region 40". Desirably the barrier 20" will extend above the periphery 28" by about 20% to about 100% of the caliper of the periphery 28", and preferably from about 25% to about 50%.

Several alternative embodiments of sanitary napkins which can be provided with a medial absorbent protuberance and barrier are shown and described in U.S. Pat. No. 5,219,341 issued to Serbiak et al. on Jun. 15, 1993, U.S. patent application Ser. No. 08/263,178 filed on Jun. 21, 1994 in the name of Couture-Dorschner et al. and U.S. patent application Ser. No. 08/058,249 filed on May 12, 1993 in the name of Hirt et al.

The disclosures of all patents, patent applications, and test methods disclosed herein are hereby incorporated by reference herein and made a part hereof.

In preparing to use the above-described sanitary napkin generally an adhesive 52, as seen in FIG. 1, is secured to the garment facing side of the baffle 16. The garment adhesive 52 is used to secure the sanitary napkin 10 to the crotch portion of an undergarment during use. To protect the adhesive 52 prior to use, a release liner 54 is provided and removably affixed to the adhesive. Suitable attachment adhesives and release liners are well known in the art. For example, the attachment adhesive can be made from any know pressure-sensitive adhesive material. As used herein the term "pressure-sensitive" refers to any releasable adhesive or releasable tenacious means well known to those skilled in the art. Adhesive compositions suitable for sanitary napkins include, for example, styrenic polymers such as styrene ethyl butylene styrene. The adhesive attachment means can also comprise two sided adhesive tape.

While the particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. An absorbent article having an outer perimeter, said article comprising;
   a) a bodyfacing liquid-permeable cover;
   b) a garment faring liquid-impermeable baffle;
   c) an absorbent core disposed between said cover and said baffle, said absorbent core having a periphery inward from said outer perimeter and an absorbent protuberance which extends above a plane parallel to said periphery; and
   d) barrier means encircling said protuberance for intercepting body fluid migrating toward said outer perimeter, said barrier means being positioned between said periphery and said outer perimeter and having a height of between about 2 millimeters to about 25 millimeters, said barrier means having horizontal channel proximate said absorbent core partially dividing said barrier means into a too section and a bottom section wherein said absorbent core partially resides between top and bottom sections, said barrier means being sufficiently compressible so that a force of about 0.1 psi to about 2 psi is needed to compress said barrier at least 50 percent and said absorbent article having a flexure -resistance of less than about 1 kilogram.

2. The absorbent article of claim 1 wherein said protuberance is medially positioned along a longitudinal central axis of said absorbent article.

3. The absorbent article of claim 1 wherein said barrier means is positioned adjacent to said periphery of said absorbent core thereby delimiting said absorbent core.

4. The absorbent article of claim 1 wherein said cover overlies said barrier means.

5. The absorbent article of claim 1 wherein said absorbent core has a predetermined thickness at said periphery and said barrier means has a height at least equal to said thickness.

6. The absorbent article of claim 1 wherein a force of about 0.3 psi to about 1.7 psi is needed to compress said barrier at least 50 percent.

7. The absorbent article of claim 6 wherein a force of about 0.5 psi to about 1.5 psi is needed to compress said barrier at least 50 percent.

8. The absorbent article of claim 1 wherein said barrier means has a width of between about 3 mm to about 12 mm.

9. The absorbent article of claim 8 wherein said barrier is a hydrophilic cellulosic sponge.

10. The absorbent article of claim 9 wherein said barrier is a cellulosic sponge compressed to about 50% of its original height dimension before incorporating into said absorbent article.

11. The absorbent article of claim 8 wherein said barrier means is a resilient, liquid-impermeable, foamed polymeric material having a density of about 0.02 grams/cm$^3$ to about 0.1 grams/cm$^3$.

12. The absorbent article of claim 1 wherein said absorbent core has a density gradient in the Z-direction wherein absorbent material forming said protuberance has a lower density relative to absorbent material positioned adjacent to said baffle.

13. An absorbent article having an outer perimeter, said absorbent article comprising:
   a) a bodyfacing liquid-permeable cover;
   b) a garment facing liquid-impermeable baffle;
   c) an absorbent core disposed between said cover and said baffle and adapted to absorb at least 5 grams of fluid, said absorbent core having a outer periphery inward from said outer perimeter and a longitudinally oriented protuberance which extends above a plane parallel to said periphery; and
   d) barrier means encircling said protuberance for intercepting body fluid migrating toward said outer perimeter, said barrier means being positioned between said outer perimeter and said periphery and having a height of between about 2 millimeters to about 25 millimeters thereby forming a gasket between a wearer's thighs and a portion of said absorbent core when said absorbent article is in use, said barrier means having a horizontal channel proximate said absorbent core partially dividing said barrier means into a top section and a bottom section wherein said absorbent core partially resides between said top and bottom sections, said barrier means being sufficiently compressible so that a force of about 0.3 psi to about 1.7 psi is needed to compress said barrier at least 50 percent and said absorbent article having a flexure-resistance of less than about 1 kilogram.

14. The absorbent article of claim 13 wherein said barrier means is positioned adjacent to said periphery of said absorbent core thereby delimiting said absorbent core.

15. The absorbent article of claim 13 wherein said periphery of said absorbent core has a predetermined thickness and said barrier means has a height at least equal to said thickness of said periphery.

16. The absorbent article of claim 13 wherein said barrier means is a resilient, liquid-impermeable, foamed polymeric material having a density of about 0.02 grams/cm$^3$ to about 0.1 grams/cm$^3$.

17. The absorbent article of claim 13 wherein said barrier means is a hydrophilic compressed cellulosic sponge material.

18. The absorbent core of claim 13 further comprising a second absorbent layer positioned between said cover and said baffle, said second absorbent layer having an absorbent density greater than said protuberance.

19. The absorbent core of claim 18 further comprising a third absorbent layer positioned between said second absorbent layer and said baffle, said second absorbent layer having an aperture for fluid communication between said protuberance and said third absorbent layer said protuberance and said aperture are coaxially aligned along a central longitudinal axis of said absorbent article.

20. The absorbent article of claim 13 wherein said barrier means has a width of between about 3 mm to about 12 mm.

21. A sanitary napkin having an outer perimeter, said sanitary napkin comprising:

a) a bodyfacing liquid-permeable cover;

b) a garment faring liquid-impermeable baffle;

c) an absorbent core disposed between said cover and said baffle, said absorbent core having a periphery with a predetermined thickness positioned inward from said outer perimeter, said absorbent core having a medially positioned, longitudinally oriented protuberance which extends above a plane parallel to said periphery; and d) a polymeric foam barrier encircling and delimiting said absorbent core, said foam barrier is selected from polyurethane, polyethylene, polypropylene and combinations thereof having a density of about 0.02 grams/$cm^3$ to about 0.1 grams/$cm^3$, said foam barrier having a horizontal channel proximate said absorbent core partially dividing said foam barrier into a top section and a bottom section wherein said absorbent core partially resides between said top and bottom sections.

22. The sanitary napkin of claim 21 wherein said protuberance has a length of about 1.5 cm to the length of said absorbent core, a width of about 1 cm to about 6 cm and a height of about 3 cm to about 25 cm.

23. The absorbent article of claim 1 wherein said barrier means is hydrophobic.

* * * * *